United States Patent [19]

Bradberry

[11] 4,105,120

[45] Aug. 8, 1978

[54] MINIATURE DENTAL KIT

[76] Inventor: Carl Bradberry, 1509 W. Farwell Ave., Chicago, Ill. 60626

[21] Appl. No.: 745,241

[22] Filed: Nov. 26, 1976

[51] Int. Cl.$^2$ .................. A45D 44/18; A61C 15/00
[52] U.S. Cl. .................. 206/581; 132/84 A; 132/92 R
[58] Field of Search ........... 206/581, 229; 132/92 R, 132/84 R, 84 A, 84 B, 84 D

[56] References Cited

U.S. PATENT DOCUMENTS

| | | | |
|---|---|---|---|
| 2,784,722 | 3/1957 | Chamberlin et al. | 132/92 R |
| 3,847,168 | 11/1974 | Schlegel | 132/92 R |
| 3,848,613 | 11/1974 | Sheehan | 132/92 R |
| 3,902,509 | 9/1975 | Tundermann et al. | 206/229 |
| 4,004,599 | 1/1977 | Rosenfeld | 132/92 R |

Primary Examiner—Herbert F. Ross
Attorney, Agent, or Firm—Hill, Gross, Simpson, Van Santen, Steadman, Chiara & Simpson

[57] ABSTRACT

A miniature dental kit comprises a handle having a pair of spaced apart arms which support a strip of dental floss. The handle is constructed to include a chamber with an opening opposite the arms for removable storage of a miniature tooth scrubber. The tooth scrubber includes a handle which may be a folded paper construction and which carries a scrubbing member impregnated with a dentifrice which is activated by saliva for scrubbing the teeth. Preferably, the entire construction is composed of biodegradeable materials and may be packaged in single or multiple units within a hygienically sealed package.

1 Claim, 4 Drawing Figures

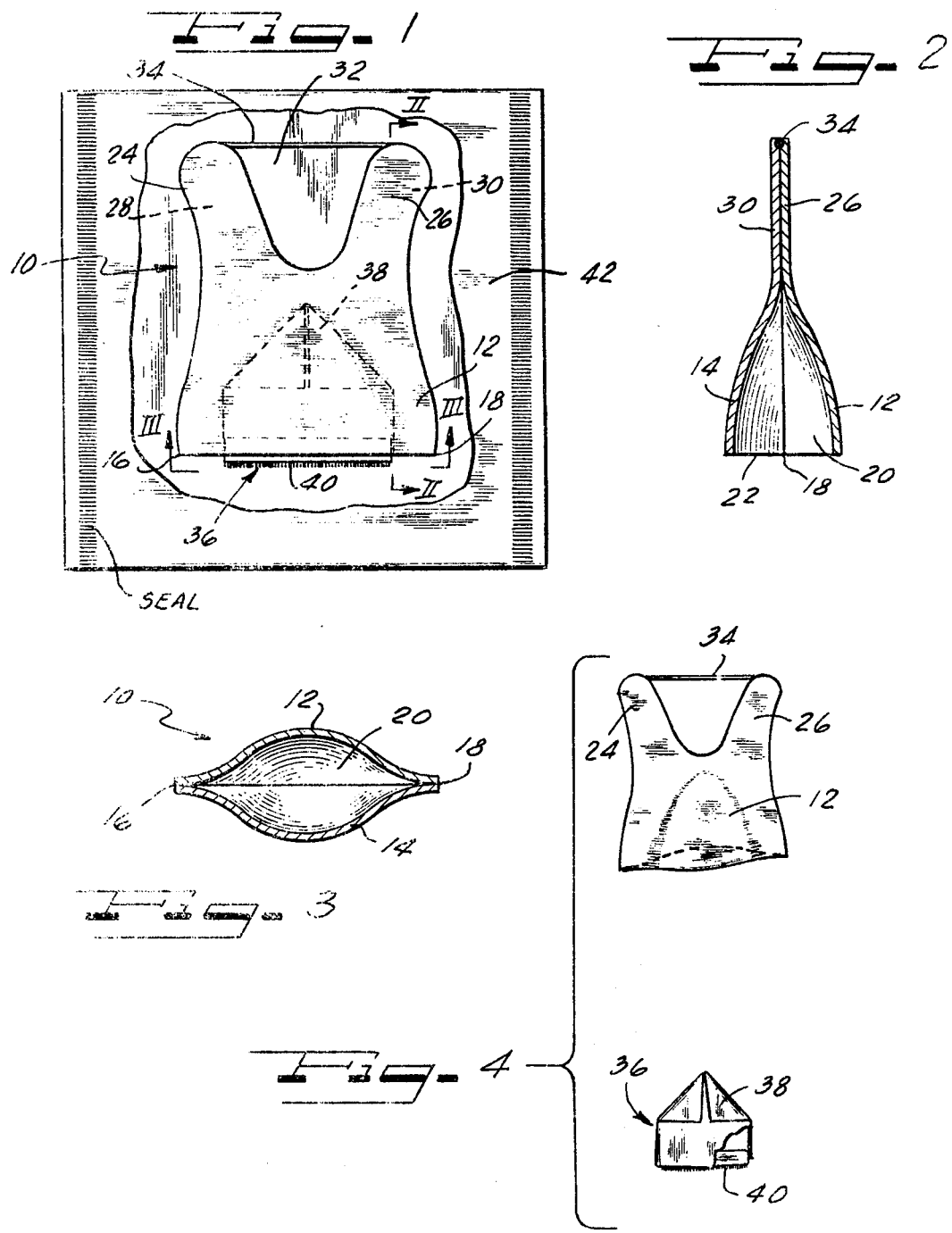

MINIATURE DENTAL KIT

BACKGROUND OF THE INVENTION

1. Field of the Invention

This invention relates to dental hygiene apparatus, and is more particularly concerned with a disposal tooth scrubber and flossing apparatus.

2. Description of the Prior Art

Various structures have heretofore been proposed which are in the nature of tooth brushes having a self-contained supply of a dentifrice. These items are generally used for travel and are often purchased from vending machines. Although some of these devices are reusable, they are generally designed for a single use and subsequent disposal.

Similarly, aids for flossing, in the form of floss-holding handles, are well known in the art and are available in the market in a variety of forms. One of these devices is designed for reuse and carries a supply of dental floss on a spool. Another of these devices is designed for a single, and perhaps several uses, but it is intended that this device be discarded in that there is no provision to reload floss.

Although some of the flossing devices are of small structure, in the main the dental hygiene toothbrushes and flossing devices are not particularly small and are not packaged together.

Also, and most important, the prior art dental hygiene devices are not biodegradable and thus contribute to the consumption of natural resources.

SUMMARY OF THE INVENTION

The primary object of the present invention is to provide a kit for dental hygiene including a tooth scrubber and a flosser in which the flosser also provides a storage chamber for the tooth scrubber.

Another object of the invention is to provide a dental kit of the type just mentioned which can be packaged singly, or several units at a time, in hygienically sealed packages.

Another object of the invention is to provide a disposal dental kit which includes a flosser and a tooth scrubber.

Still another object of the invention is to provide a dental hygiene kit in which, at least for the most part, the components are constructed of biodegradeable materials.

According to the invention, a dental flosser is constructed from a pair of sheets of material, preferably biodegradeable material such as biodegradeable paper, the sheets being superimposed one upon the other and having a pair of arm portions extending in a spaced apart relationship. The sheets of material are coextensive and are bonded together along the greatest part of their periphery to form an opening which leads to a storage chamber for storing a tooth scrubber as detailed below. A strip of dental floss is secured to the distal ends of the arms and the bonded sheets constitute a handle for manipulating the dental floss about the teeth.

A tooth scrubber includes a handle, preferably also of biodegradeable material, and carries a scrubbing member which has a supply of dentifrice, such as tooth powder or the like, which is activated by the saliva within the mouth. The tooth scrubber is removably stored in the chamber of the envelope formed by the two sheets of the flosser and may easily be withdrawn for use.

A particularly novel feature of the invention, and one especially favorable in enticing children to practice good dental hygiene, resides the provision of the two sheets of material in the outline of a tooth such that the primary portion of the flosser represents the intermediate and crown areas of a tooth, for example a molar, while the extending arms represent roots of the tooth.

BRIEF DESCRIPTION OF THE DRAWINGS

Other objects, features and advantages of the invention, its organization, construction and operation will be best understood from the following detailed description, taken in conjunction with the accompanying drawings, on which:

FIG. 1 is an elevational view of a miniature dental kit constructed in accordance with the teachings of the present invention;

FIG. 2 is a sectional view taken substantially along the line II—II of FIG. 1;

FIG. 3 is an end view as seen looking in the direction III—III of FIG. 1; and

FIG. 4 is an exploded view of the apparatus of FIG. 1.

DETAILED DESCRIPTION OF A PREFERRED EMBODIMENT

Referring to the drawing, a dental hygiene kit is generally illustrated at 10 as comprising a pair of sheets of material 12 and 14, in the shape of a tooth, and preferably consisting of biodegradeable material. The sheets 12 and 14 are coextensive and are bonded together about the greatest distance of the periphery between the points 16 and 18, such as by gluing or the like, to form a chamber or envelope 20 therebetween. The envelope 20 constitutes a storage chamber for a tooth scrubbing means 36 which is detailed hereinbelow. The sheets are not bonded together along the lesser portion of the periphery between the points 16 and 18 to form an opening 22 through which the tooth scrubber 36 is received into and withdrawn from the envelope 20.

The sheet 12 includes a pair of arm portions 24 and 26 extending in a spaced apart relation, while the sheet 14 includes a comparable pair of arm portions 28 and 30 which are coextensive with the arm portions 24 and 26 and, when bonded thereto, form a pair of arms which carry a strip of dental floss 34 which is secured to the distal ends thereof. The floss 34 can be secured to the arms at the time the sheets 12 and 14 are bonded together.

The two arms and the strip of dental floss form the outline of an area 32 which is not particularly critical. It is readily apparent, however, that the spacing of the arms should be sufficient to bridge the teeth of a user and the depth of the area from the floss 34 to the main body of the "tooth" should be sufficient to permit complete entry of the floss to the gum line.

The tooth scrubber 36 comprises a handle 38 which may be constructed of a folded sheet of biodegradeable material, such as biodegradeable paper. The folded construction may advantageously be in the form of an envelope which has a scrubbing member 40 secured therein and extending therefrom. The scrubbing member 40 may carry, such as by impregnation, a dentifrice, or a dentifrice may be housed within the envelope of the handle 38. Preferably, the scrubbing member 40 has a bristle character over the outer portion which engages the teeth and the dentifrice may be activated by saliva.

In a preferred form, the dental kit, as illustrated in FIG. 1, is hygienically sealed in a package 42 which is preferably of a transparent material. Several such packages may be affixed together in a perforate tear-off strip of dental kits so that the kits may be individually used, but purchased in groups.

It should be noted that it is not necessary to construct the handles of the flosser and the scrubber from biodegradeable materials, although such construction is preferred. Plastics may be used for the handles. Also, it is not necessary to utilize two coextensive sheets to form the handle of the flosser; a single sheet with a non-coextensive pouch attached thereto may suffice. It should be noted that when two coextensive sheets are utilized and bonded together, it may be advantageous to permit the bonding material to cover the entire arm area so as to provide additional rigidity for the flosser.

The invention has various beneficial and advantageous features in addition to those set forth above. For example, the tooth scrubber may also be employed to massage the gums. In this connection, and inasmuch as the components of the dental kit are used in the mouth and applied by hand, it will be appreciated that there are no sharp points to cause injury to any person who may use the dental kit. Also, the dental kit may be safely carried in the pocket or in a purse without causing injury when the user reaches for the same. Therefore, the dental kit is safe for storage, transport and use by all individuals, from infant to adult.

From the foregoing it is readily apparent that a dental kit constructed in accordance with the present invention, and preferably constructed of biodegradeable materials, can be used anywhere, e.g. at home, in the office, in vehicles or in the open, and the components thereof may be readily disposed of by discarding the same in waste receptacles, or the same may be flushed down a toilet.

Although I have described my invention by reference to particular embodiments thereof, many changes and modifications of the invention may become apparent to those skilled in the art without departing from the spirit and scope of the invention. I therefore intend to include within the patent warranted hereon all such changes and modifications as may reasonably and properly be included within the scope of my contribution to the art.

I claim:

1. Dental hygiene kit comprising:

a pair of sheets of biodegradeable paper material each including a pair of spaced apart arm portions shaped in the form of a tooth with said arms representing roots extending from one end of said kit, said sheets disposed in a superimposed coextending relation and bonded together along their marginal edges to form a chamber therebetween at the other end of said kit, said chamber having an opening in the marginal edge at said other end;

a strip of dental floss permanently secured between the distal ends of said arms, said bonded sheets constuting a first handle for use in applying said dental floss to the teeth; and tooth scrubbing means disposed in said chamber and removable therefrom through said opening, said tooth scrubbing means including a dentifrice, a scrubbing member carrying said dentifrice and a second handle of biodegradeable material carrying said scrubbing member.

* * * * *